(12) United States Patent
Goldberg

(10) Patent No.: US 8,403,882 B2
(45) Date of Patent: Mar. 26, 2013

(54) APPLICATOR DEVICE FOR APPLYING A MULTI-COMPONENT FLUID

(75) Inventor: Edit Goldberg, Zichron Yaakov (IL)

(73) Assignee: Omrix Biopharmaceuticals, S.A., Rhode-St.-Genese (BE)

( * ) Notice: Subject to any disclaimer, the term of this patent is extended or adjusted under 35 U.S.C. 154(b) by 135 days.

(21) Appl. No.: 11/718,951

(22) PCT Filed: Nov. 22, 2005

(86) PCT No.: PCT/EP2005/056154
§ 371 (c)(1),
(2), (4) Date: May 9, 2007

(87) PCT Pub. No.: WO2007/059801
PCT Pub. Date: May 31, 2007

(65) Prior Publication Data
US 2009/0076459 A1    Mar. 19, 2009

(51) Int. Cl.
*A61M 37/00* (2006.01)
(52) U.S. Cl. .............. 604/82; 604/83; 604/89; 604/90; 604/91; 604/191
(58) Field of Classification Search .............. 604/82, 604/83, 89–91, 191; 222/137
See application file for complete search history.

(56) References Cited

U.S. PATENT DOCUMENTS

| | | |
|---|---|---|
| 4,359,049 A | 11/1982 | Redl et al. |
| 5,104,375 A | 4/1992 | Wolf et al. |
| 5,290,259 A * | 3/1994 | Fischer .................. 604/218 |
| 5,759,171 A | 6/1998 | Coelho et al. |
| 6,113,571 A * | 9/2000 | Zinger et al. .................. 604/82 |
| 6,113,573 A | 9/2000 | Phillips |
| 6,234,994 B1 * | 5/2001 | Zinger .......................... 604/82 |

(Continued)

FOREIGN PATENT DOCUMENTS

| | | |
|---|---|---|
| DE | 29509729 | 8/1995 |
| EP | 0689874 | 6/1996 |

(Continued)

OTHER PUBLICATIONS

"Translation of WO-95/31137"—PDF of Machine Translation result from EPO website.*

*Primary Examiner* — Bhisma Mehta
*Assistant Examiner* — Larry R Wilson
(74) *Attorney, Agent, or Firm* — David R. Crichton

(57) ABSTRACT

Disclosed is an applicator device (10) for applying a multi-component fluid, especially a multi-component tissue glue, comprising a plurality of substantially cylindrical supply containers (12) for respectively one component of the fluid to be applied, each supply container (12) having a front end (16) with an outlet opening (18), a rear end (22) opposite to the front end (16), and a slidably displaceable piston (24) arranged within the supply container (12) and having a piston rod (26) extending out of the rear end (22) for operating the piston (24). Moreover, the applicator device includes a manifold (72) having terminal ends (50,58) with a first port for fluid connection with the front ends (16) of the supply containers (12), the manifold (72) further having internal channels (62) extending from the first ports of the terminal ends (50,58) to an outlet site. Finally, also a holding element (38) for holding the supply containers (12), and a coupling element (74) extending from the holding element (38) and having a connection end (76) connected to the manifold (72) are provided, wherein the connection end (76) of the coupling element (74) is bonded to the manifold (72).

8 Claims, 3 Drawing Sheets

U.S. PATENT DOCUMENTS

| | | |
|---|---|---|
| 6,357,489 B1 | 3/2002 | Zinger |
| 6,568,434 B2 | 5/2003 | Zinger |
| 7,635,343 B2 * | 12/2009 | McIntosh et al. .......... 604/82 |
| 2002/0068907 A1 | 6/2002 | Dysarz |
| 2003/0233067 A1 | 12/2003 | McIntosh et al. |
| 2005/0101963 A1 | 5/2005 | Merboth et al. |

FOREIGN PATENT DOCUMENTS

| | | |
|---|---|---|
| EP | 0925062 | 6/1999 |
| EP | 0814866 | 6/2001 |
| EP | 0925026 | 2/2003 |
| EP | 0925065 | 9/2005 |
| JP | 2001-504716 | 4/2001 |
| JP | 2002-512536 | 4/2002 |
| JP | 2003-250806 | 9/2003 |
| WO | 95/31137 | 11/1995 |
| WO | WO 9531137 A1 * | 11/1995 |
| WO | 98/10703 | 3/1998 |
| WO | 98/10704 | 3/1998 |
| WO | 01/32242 | 2/2001 |
| WO | 02/05898 | 1/2002 |
| WO | 03/105933 | 12/2003 |
| WO | 2007/059801 | 5/2007 |

* cited by examiner

APPLICATOR DEVICE FOR APPLYING A MULTI-COMPONENT FLUID

BACKGROUND OF THE INVENTION

1. Field of the Invention

The present invention relates to an applicator device for applying a multi-component fluid. In particular, the present invention relates to an applicator device for applying a multi-component tissue glue for surgical purposes.

2. Related Prior Art

Applicator devices for applying a multi-component fluid and, in particular, a multi-component tissue glue are known. One example of such an applicator device is described e.g. in U.S. Pat. No. 6,113,573 and in EP-B-0 925 062. This known type of tissue glue applicator device comprises a plurality of substantially cylindrical supply containers in the form of syringes for respectively one component of the fluid to be applied. Each of the supply containers has a front end with an outlet opening, a rear end opposite to the front end, and a slidably displaceable piston arranged within the supply container and having a piston rod extending out of the rear end for operating the piston. The supply containers are connected to terminal ends of the manifold which comprises internal channels extending from the terminal ends to an outlet site of the manifold. Moreover, the known type of tissue glue applicator comprises a holding element for holding the supply containers.

This kind of applicator device basically works satisfactorily. In order to prevent popping off of the manifold from the supply containers due to clogging of its channels, WO-A-98/10704 and U.S. Pat. No. 6,234,994 each disclose a coupling element mechanically attached to the manifold and connected to the holding element. By this known coupling element, the manifold is securely attached to the outlet openings of the supply containers. Other examples for securing the manifold to the supply containers by coupling elements and the like connected to the supply container holding element are disclosed in WO-A-95/31137, WO-A-02/05898, WO-A-03/105933, EP-B-0 689 874, U.S. Pat. Nos. 4,359,049, 5,104,375, 5,290,259, US-A-2003/0 233 067, and DE-U-295 09 729.

The known tissue glue applicator devices are provided with a catheter extending from the manifold and provided with one or several lumina in fluid communication with the internal channels of the manifold. Depending on the purposes for which the tissue glue applicator is used, the catheter can have a significant length. The longer the catheter, the more torque the catheter applies to the manifold. As it turned out in practice, the known concepts of securing the manifold to the supply containers and the holding elements thereof might not be stable enough when used for manifolds having a rather long catheter.

Accordingly, there is a need for an improved construction of an applicator device for applying a multi-component fluid, especially a multi-component tissue glue.

SUMMARY OF THE INVENTION

The present invention provides an applicator device for applying a multi-component fluid, especially a multi-component tissue glue, comprising a plurality of substantially cylindrical supply containers for respectively one component of the fluid to be applied, each of said supply containers having a front end with an outlet opening, a rear end opposite to the front end, and a slidably displaceable piston arranged within said supply container and having a piston rod extending out of said rear end for operating the piston, a manifold having terminal ends with a first port for fluid connection with the front ends of said supply containers, said manifold further having internal channels extending from said first ports of said terminal ends to an outlet site, holding elements for holding said supply containers, and a coupling element extending from said holding element and having a connection end connected to said manifold, wherein said connection end of said coupling element is bonded to said manifold.

The applicator device according to the present invention is provided with a coupling element for mechanically connecting the manifold to the holding element for the supply containers. According to the invention, the coupling element is bonded to the manifold. In one aspect of the present invention, the coupling element is glued to the manifold. As an alternative and according to another embodiment of the present invention, the coupling element is welded to the manifold. Typically, the manifold and the coupling element are made from plastics material of the same kind or a different kind. Accordingly, the glue used is to be adapted to the specific plastics material combination of the manifold and the coupling element. If bonding is performed by welding, in particular an ultrasonic welding connection can be used. If a glue connection is used, curing the glue can be performed by exposing the glue to air or a specific gas or to a specific curing radiation. The glue and welding connection, i.e. the bond between the manifold and the coupling element, should withstand normal operating conditions and should be stable for the lifetime of the applicator device.

In another aspect of the present invention, the manifold comprises a housing having the terminal ends of the manifold extending from the housing wherein the connecting end of the coupling element at which the coupling element is bonded to the housing of the manifold, is arranged between and bonded to at least two adjacent terminal ends of the manifold. This kind of connection requires only little space. If the manifold comprises two terminal ends for connecting the manifold to the outlet ends of two supply containers, the coupling element is preferably aligned with the two terminal ends of the manifold.

The terminal ends of the manifold are provided with first parts for providing fluid communication with the outlet ends of the supply containers. In a preferred embodiment of the present invention, said terminal end of said manifold is provided with a second port capable of selectively being in fluid communication with the channel extending from the first port of said terminal end, and a fluid communication control element selectively operable in a first flow control position for providing a fluid communication between said first port and said second port, and in a second fluid control position for providing a fluid communication between the second port and said outlet site of said manifold. The fluid communication control element used according to this embodiment of the present invention basically is described e.g. in EP-B-0 814 866 as well as in EP-B-0 925 065 and U.S. Pat. No. 6,113,571. The disclosure of these three references is incorporated herewith by reference. Operating the applicator device disclosed in these three references is described in more detail in U.S. Pat. Nos. 6,357,489 and 6,568,434, the disclosure of which is also incorporated herein by reference.

Typically, in order to spray the discharged multi-component fluid, the manifold comprises a further terminal end provided with a hose or the like conduit providing a gaseous substance (medical gas like oxygen) from the terminal end to the outlet site. As referred to above, the outlet site can be arranged at the housing of the manifold or at the one end of a single or multi-lumen catheter attached to the housing and extending therefrom with the one or multi-lumen in fluid communication with the individual channels of the manifold. However, these channels can be separated or combined into one channel within the manifold.

In another preferred embodiment of the present invention, the manifold is connected by means of Luer lock connectors to the terminal ends provided with the fluid communication control elements as described above. This is advantageous in that a manifold which during intermediate operation of the applicator device might be clogged due to cured tissue glue, can be replaced without the need of disposing the whole applicator device.

The main aspect of the present invention resides in the stable connection of the holding element to the manifold. According to the invention, this is performed by a glue or weld connection which is much more stable than a known clamping connection of the prior art applicator devices.

BRIEF DESCRIPTION OF THE DRAWINGS

The present invention will be described in more detail hereinbelow referring to the drawings, in which.

DETAILED DESCRIPTION OF PREFERRED EMBODIMENTS OF THE INVENTION

Figure 1:
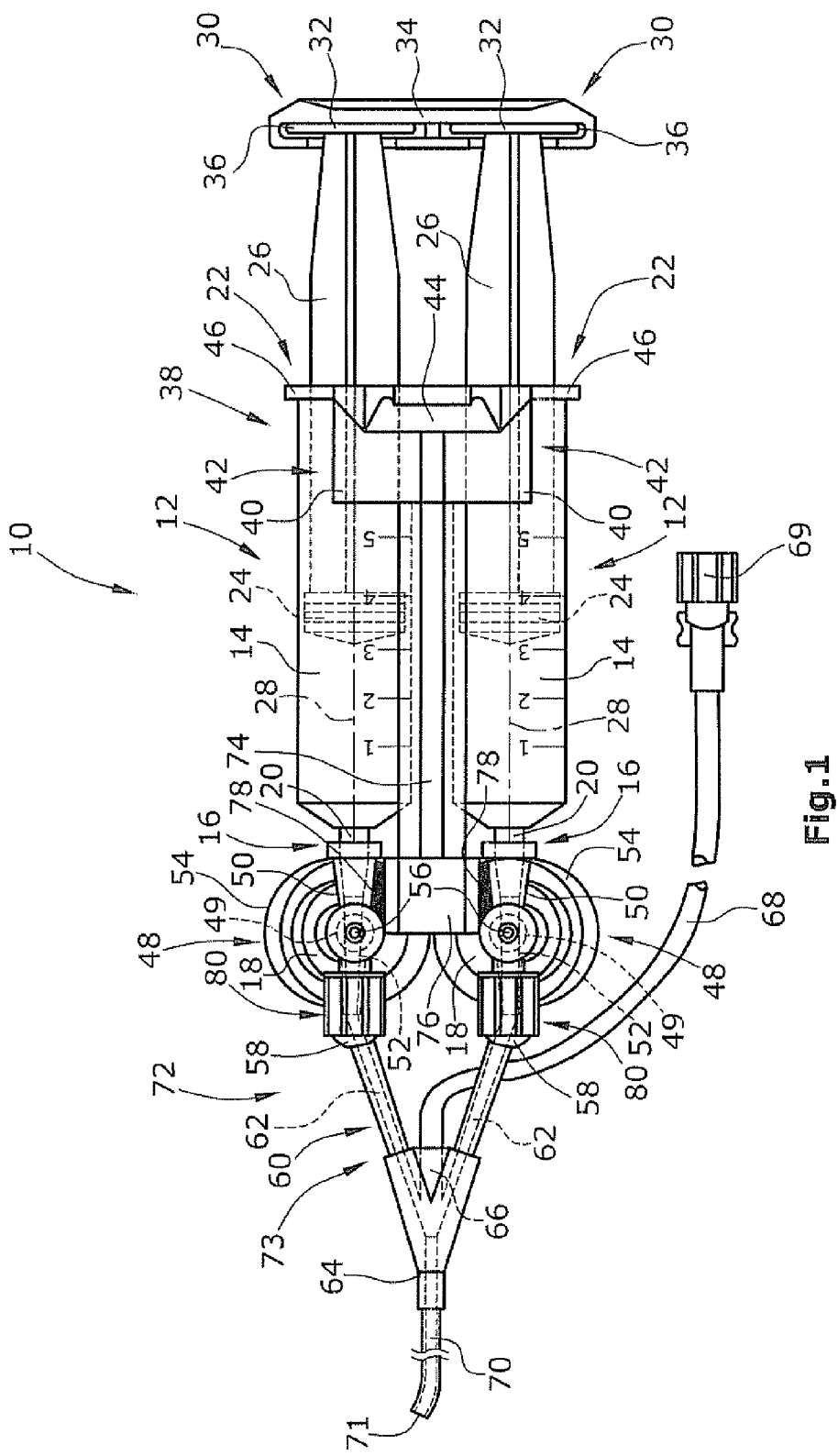
FIG. 1 shows a plan view of a tissue glue applicator device according to a first embodiment.

FIG. 1 shows a plan view of an applicator device 10 for multi-component tissue glues. Applicator device 10 comprises two supply containers provided as commercially available syringes 12 for solutions of proteins, such as fibrinogen, and of fibrinolytic substances, such as thrombin, of a two-component tissue glue. Each syringe 12 comprises a hollow cylindrical syringe body 14 having a front end 16 with an outlet opening 18 and connecting pieces 120, and an open rear end 22. Arranged in each syringe body 14 is a piston 24 in sealing abutment on the inner surface of syringe body 14. Piston 24 is held by a piston rod 26 guided out of syringe body 14 through the rear end 22. The piston rods 26 extend respectively in the longitudinal direction of the syringe bodies 14 (cf. the longitudinal axes 28 of the syringe bodies 14 indicated in the drawings). The free ends 30 of piston rods 26 facing away from piston 24 have annular flanges 32 formed thereon. These annular flanges 32 are mechanically connected to each other by a coupling element 34. Coupling element 34 is formed with two receiving recesses 36 which are laterally open and suited for insertion of the annular flanges 32 thereinto.

As shown in FIG. 1, the two syringe bodies 14 are connected to each other by a clip holding means 38 (hereinbelow referred to as a holding element). Holding element 38 comprised two C-shaped holding clamps 40 of which the openings 42 are facing away from each other and which are connected to each other by their middle portions ("back portions"). The openings 42 are oriented in the direction of the extension of that plane (here coinciding with the plane of FIG. 1) in which the longitudinal axes 28 of the syringe bodies 14 are arranged. The clamps 40 are provided with two under-grip-projections 44. (In the view of FIG. 1, only one projection 44 is visible.) These projections 44 extend in mutually opposite directions, being arranged at a rotational displacement of 90° relatively to the two clamps 40 or respectively their openings 42. Thus, the two projections 44 respectively project at right angles from the plane (of FIG. 1) in which the longitudinal axes 28 of the syringe bodies 14 are held by the holding element 38, or respectively in which the longitudinal axes of the clamps 40 extend, coinciding with the longitudinal axes 28 of the syringe bodies 14. This means that the projections 44 protrude in opposite directions along the axis of symmetry of the twin clamp arrangement.

The holding clamps 40 may extend by about 180° around the syringe bodies 14 and may enclose the syringe bodies 14 with a clamping force. The holding element 38 receives laterally protruding flanges 46 on the rear ends 22 of the syringe bodies 14, thus axially securing the syringe bodies 14. The axial dimension of holding element 38 and especially of the holding clamps 40 is such that the scale markings arranged externally on the syringe bodies 14 are left unobstructed and are not covered by the holding element 38.

As evident from FIG. 1, the slightly conical connecting pieces 20 on the front ends 16 of the syringe bodies 14 are respectively connected to a fluid control device 48. Each fluid control device 48 is provided with a connector 50 receiving the conical connecting piece 20 of a syringe both 14. Each fluid control device 48 is provided with an outlet connecting piece 52 opposite to connector 50. Further, each fluid control device 48 is provided with a receiving adaptor 54 comprising a fluid conduit member 56. The receiving adaptor 54 is configured for insertion of a medicinal vessel thereinto, with the fluid conduit member, formed as a puncturing needle, penetrating the rubber closure plug of the vessel and extending into the interior of the vessel. Each fluid control device 48 has a flow control member (shown in FIG. 1 at 49) rotatably supported therein. This flow control member can be rotated from outside, which is performed particularly by rotating the adaptor 54. By rotating the flow control member, the flow control member can be moved from a first fluid control position wherein a fluid path exists between a syringe body 14 and the medicinal vessel, into a second fluid control position wherein the syringe body 14 is in fluid connection with the outlet connecting piece 52 of fluid control device 48. The structure and the function of each fluid control device 48 and their use for loading the syringes 12 of the applicator device 10 with the fluid components as well as for displacing them are explained in greater detail in U.S. Pat. No. 6,113,571, EP-B-0 925 026, EP-B-0 814 866, U.S. Pat. Nos. 6,357,489 and 6,568,434, the disclosures of which are incorporated herein by reference.

The outlet connecting pieces 52 of fluid control device 48 have the connectors 58 of a connecting headpiece 60 mounted thereon. The connecting headpiece 60 is formed with channels 62 extending therethrough for connecting said connectors 58 to the outlet end 64 of connecting headpiece 60. Further, the connecting headpiece 60 is formed with an additional channel 66 extending therethrough and having a hose 68 for a medicinal gas, e.g. $O_2$, with an e.g. Luer lock connector 69 for connecting a source thereto. Also channel 66 extends to the outlet end 64 of connecting headpiece 60. On the outlet end 64, the connecting headpiece 60 is joined by a flexible three-lumina catheter 70 having an outlet site 71 at its free end, its three lumina being flush the inner channels 62 and 66 of connecting headpiece 60 at the outlet end 64 of headpiece 60. The fluid control devices 48 and the connecting headpiece form the manifold 72 according to a first embodiment of the applicator device 10.

Figure 2:
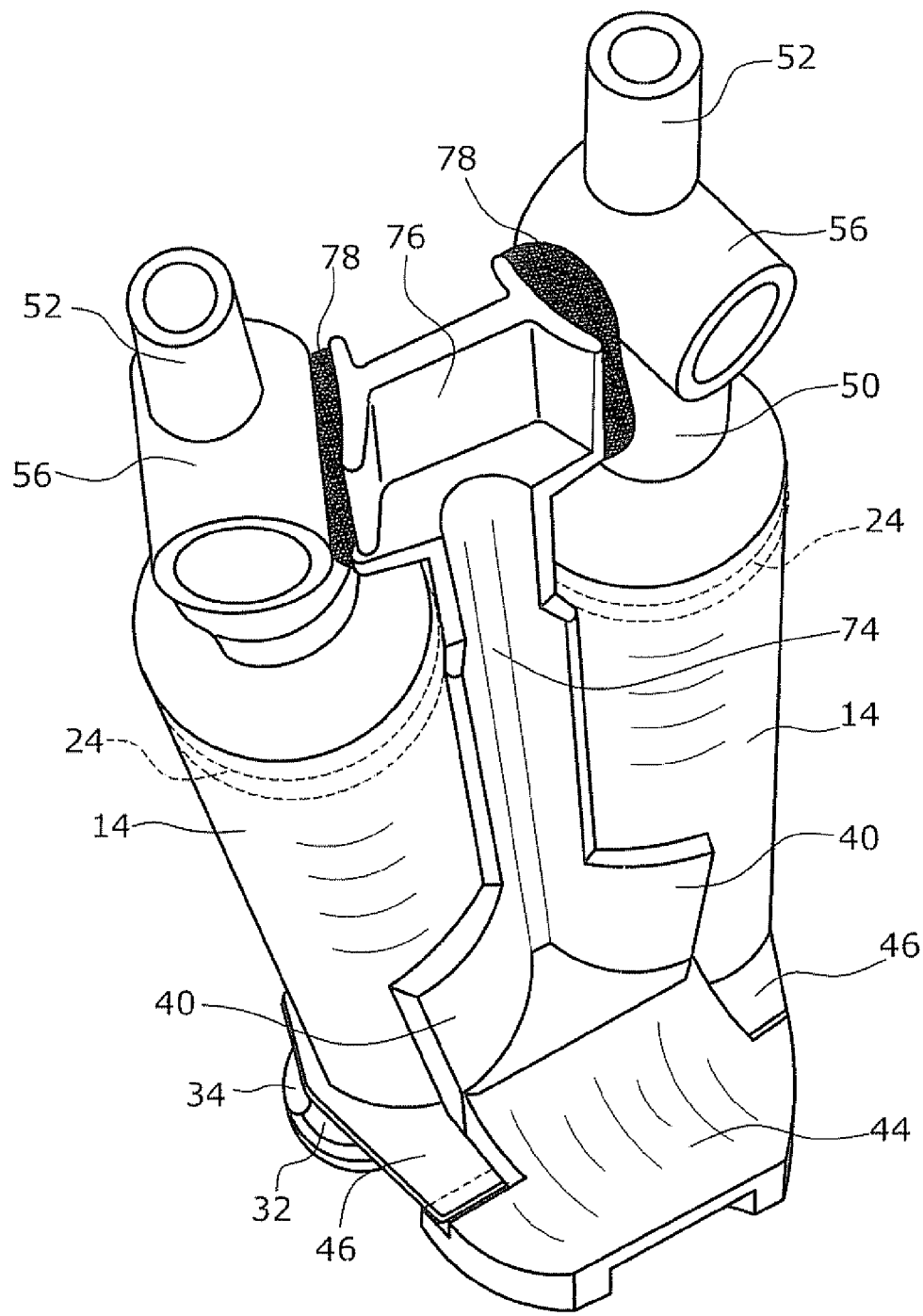
FIG. 2 shows a corresponding view of the applicator device according to FIG. 1 with a portion of the manifold being detached.

A further typical feature of the applicator 10 according to FIGS. 1 and 2 is a coupling element 74 preferably integrally connected to the holding element 38 and, in particular, to its holding clamps 40. The coupling element 74 extends between the two syringes 12 which preferably contact the coupling element 74 at opposite sides for guiding and abutment purposes. The coupling element 74 is provided with a free end 76 forming a connection end at the fluid control devices 48. In this embodiment, the connection end 76 is glued (see reference numeral 78 in FIGS. 1 and 2) to the connectors 50 of the fluid control devices 48. However, this type of connection is not the only possible bonding connection between the coupling element 74 and the manifold 72. As an alternative to gluing, also welding the connection end 76 to the manifold 72 is possible.

The strong bonding connection by gluing or welding provides additional stiffness to the overall applicator device 10, which is useful in particular in cases where the manifold 72 is provided with a rather long catheter 72, e.g. for endoscopic surgery purposes.

As also shown in FIG. 1, the connecting head piece 60 of the manifold 72 is connected to the fluid control devices 48 by means of Luer lock connectors 80. This makes it possible, in case of a potential clogging, to replace the connecting head piece 72 and catheter 70 by a new manifold and catheter.

Figure 3:
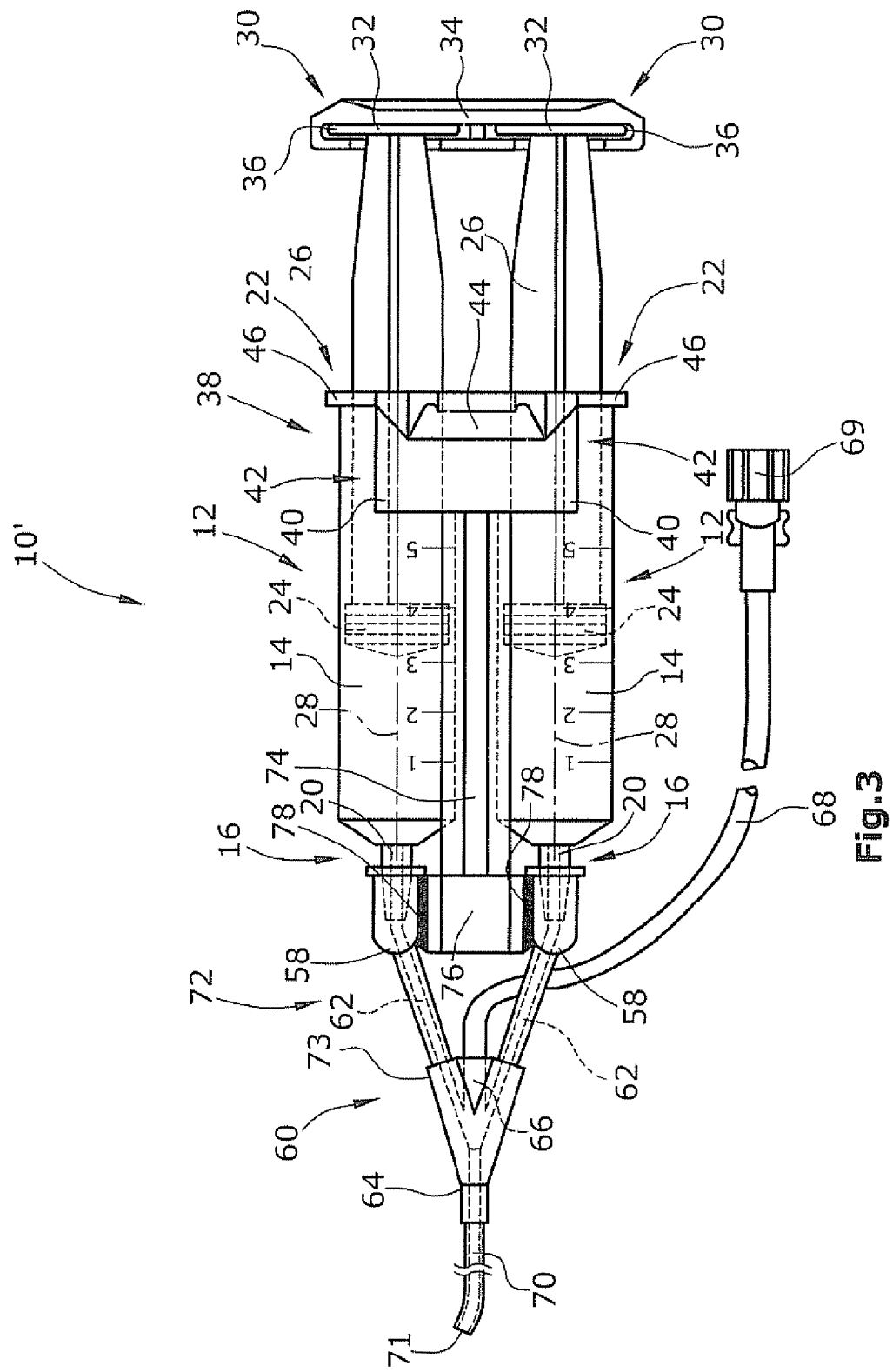
FIG. 3 shows a plan view of a second embodiment of a tissue glue applicator device.

FIG. 3 shows an alternative embodiment of a tissue glue applicator 10' which basically is identical to the applicator device 10 of FIGS. 1 and 2, except for the manifold 72 which comprises the connecting head piece and catheter 70 only, i.e. without the fluid control devices 48 shown in FIGS. 1 and 2. The bonding connection between the coupling element 74 and the manifold 72 is the same, preferably using a glue or a welding connection. In the embodiment of FIG. 3, the connection end 76 of the coupling element 74 is bonded, i.e. glued or welded, to the terminal ends 58 of the connecting head piece 60. It is to be noted that in FIG. 3 the same reference numerals are used for elements of the applicator device 10' which, regarding their structure and function, are identical or similar to corresponding elements of the applicator device 10 shown in FIGS. 1 and 2.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

The invention claimed is:

1. An applicator device for applying a multi-component fluid, especially a multi-component tissue glue, comprising
   a plurality of substantially cylindrical supply containers for respectively one component of the fluid to be applied, each of said supply containers having a front end with an outlet opening, a rear end opposite to the front end, and a slidably displaceable piston arranged within said supply container and having a piston rod extending out of said rear end for operating the piston,
   a manifold having terminal ends with a first port for fluid connection with the front ends of said supply containers, said manifold further having internal channels extending from said first ports of said terminal ends to an outlet site,
   a holding element for holding and gripping said supply containers, and
   a coupling element extending from said holding element and having a connection end connected to said manifold,
   wherein the coupling element contacts the supply containers along their longitudinal axis, and
   wherein said connection end of said coupling element is non-releasably bonded to said manifold.

2. The applicator according to claim 1, wherein said manifold comprises a housing having its terminal ends extending therefrom and wherein said connection end of said coupling element is arranged between and bonded to at least two adjacent terminal ends of said manifold.

3. The applicator according to claim 1, wherein each terminal end of said manifold is provided with a second port capable of selectively being in fluid communication with the channel extending from the first port of said terminal end, and a fluid communication control element selectively operable in a first flow control position for providing a fluid connection between said first port and said second port and in a second fluid control position for providing a fluid communication between the second port and said outlet site of said manifold.

4. The applicator device according to claim 1, wherein said manifold comprises a further terminal end and a further internal channel extending from said further terminal end to said outlet site for supplying a gaseous substance from said further terminal end to the outlet site.

5. The applicator device according to claim 2, wherein said connection end of said coupling element is glued to said manifold.

6. The applicator device according to claim 2, wherein said connection end of said coupling element is welded to said manifold.

7. The applicator device according to claim 1, wherein said coupling element is integrally formed with said holding element.

8. The applicator device according to claim 1, wherein said outlet site is provided at one end of a single of multi-lumina catheter extending from said manifold.

* * * * *

UNITED STATES PATENT AND TRADEMARK OFFICE
CERTIFICATE OF CORRECTION

PATENT NO. : 8,403,882 B2  
APPLICATION NO. : 11/718951  
DATED : March 26, 2013  
INVENTOR(S) : Edit Goldberg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 254 days.

Signed and Sealed this

First Day of September, 2015

Michelle K. Lee
*Director of the United States Patent and Trademark Office*